US00PP34502P2

(12) United States Plant Patent
Hansen

(10) Patent No.: US PP34,502 P2
(45) Date of Patent: Aug. 16, 2022

(54) ***NEPETA* PLANT NAMED 'PICTURE PURRFECT'**

(50) Latin Name: ***Nepeta* hybrid**
Varietal Denomination: 'Picture Purrfect'

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,301

(22) Filed: Apr. 28, 2022

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Karen M Redden

(57) ABSTRACT

The new and distinct hardy perennial plant, *Nepeta* 'Picture Purrfect', has a broad, low spreading mound, with compact habit with mostly upright stems. The foliage is small, serrate and fragrant. Flowers are a bluish-purple with persistent rosy-purple calyces and dark purplish-red peduncles. The new plant begins flowers about two weeks earlier than typical ornamental catnip cultivars and reblooms after initial flowering. The new plant is useful in the landscape en masse, as an accent, or in containers.

1 Drawing Sheet

Botanical denomination: *Nepeta* hybrid.
Variety designation: 'Picture Purrfect'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2021 followed by the "Walters Gardens 2021-2021 Catalog" initially released on May 21, 2021. The claimed plant was first sold on Jul. 12, 2021 to Harts Nursery, Jardins Michel, Exemplar Horticultural, and Walla Walla Nursery, as well as other nurseries afterward by Walters Gardens, Inc., who obtained the plant and all information relating from the inventor. No plants of *Nepeta* 'Picture Purrfect' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to a new and distinct cultivar of *Nepeta* named 'Picture Purrfect'. The new plant was selected as a single seedling from the progeny of self-pollination cross of the proprietary, unreleased hybrid known only as 13-13-3 (not patented). The pollination was directed by the inventor on Jun. 1, 2015, seed was harvested in the summer of 2015, grown out and evaluated, and a single seedling was selected and assigned the breeder code 15-16-1 toward the end of the trial period. 'Picture Purrfect' was approved in a final evaluation in the summer of 2019 and slated for later introduction. The new plant was selected based on the compact habit and repeat blooming following trimming. The new plant has been asexually propagated first by division in the late summer of 2017 followed by tip cuttings with the resultant plants remaining identical to the original plant, stable and true to type in successive generations.

SUMMARY OF THE INVENTION

*Nepeta* 'Picture Purrfect' is different from its parents and all other Catmint cultivars known to the inventor. The nearest comparison plants known by the inventor include: 'Cat's Meow' U.S. Plant Pat. No. 24,472, 'Cat's Pajamas' U.S. Plant Pat. No. 31,127, 'Novanepjun' U.S. Plant Pat. No. 23,074, more commonly known as 'Junior Walker', 'Kitten Around' U.S. Plant Pat. No. 30,940, 'Purrsian Blue' U.S. Plant Pat. No. 24,788, 'Psfike' U.S. Plant Pat. No. 18,904.

'Cat's Meow' is taller and broader in habit and begins flowering about one to two weeks later with smaller flowers and darker purple calyces and darker purple stems. 'Cat's Pajama's' is slightly taller, more rounded in habit and has smaller flowers with lighter purple calyces and darker purple stems. 'Novanepjun' is taller, flowers about two weeks later with flowers that are smaller and more purplish in color. 'Pursian Blue' has more purplish-blue flowers that are smaller, begin opening about two weeks later, and the habit is taller and broader. 'Psfike' has smaller flowers and the habit is not as broad and not as vigorous in growth.

The parent plant is more compact and shorter the flowers are smaller and the stems less sturdy.

The present invention has not been evaluated under all possible environmental conditions. The phenotype may vary with changes in the environment such as light, temperature, water and nutrient availability, etc. without a change in the genotype of the plant. *Nepeta* 'Picture Purrfect' is unique from all other catmint known to the inventor in the following combined traits:

1. The habit is rounded, very short and compact with mostly upright stems;
2. Foliage is small with serrate teeth and fragrant;

3. Flowers are large, bluish-purple with persistent rosy-purple calyces and dark purplish-red peduncles;
4. Plant blooms about two weeks earlier than many ornamental catnip cultivars and reblooms after initial flowering.

BRIEF DESCRIPTION OF THE DRAWINGS

The photographs of the new plant *Nepeta* 'Picture Purrfect' are of a four-year old plant in a full-sun, trial garden in Zeeland, Mich. and demonstrate the unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
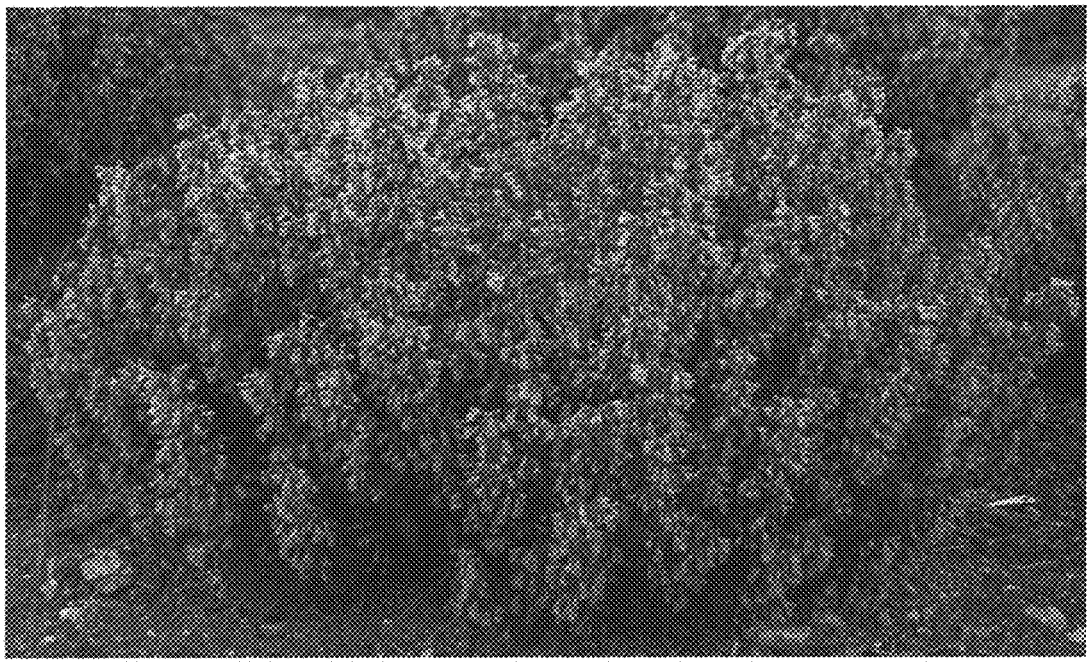
FIG. 1 shows the overall habit of the new plant.
Figure 2:
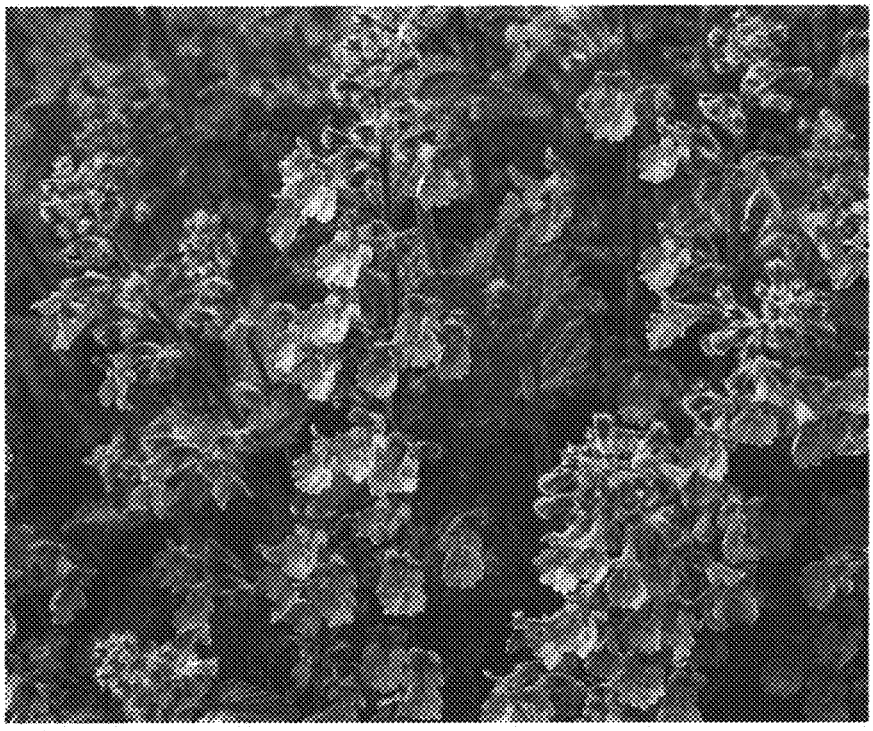
FIG. 2 shows a close-up of the flowers, buds and stems.

The following descriptions are based on a four-year old plant of *Nepeta* 'Picture Purrfect' grown in a full-sun trial garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: Self-pollination of the proprietary hybrid 13-13-3;

Plant habit: Herbaceous perennial; multi-stemmed, mounding to about 34 cm tall and 83 cm wide at the base in flower;

Growth: Rapid; time to initiate roots at 23° C. about one week; finishing in a standard #1-15 cm container in about 8 to 10 weeks from rooted 25 mm plug;

Root: Fine, freely branching; color between RHS NN155C and RHS 158D depending on soil type and nutrient content;

Foliage: Opposite; simple; ovate; rugose on both abaxial and adaxial surfaces; margins crenate with 10 to 13 teeth per side; micro-puberulent on adaxial and abaxial surfaces; apex acute; base cordate; blade size to about 38 mm long and 25 mm wide near base, average about 29 mm long and 18 mm across;

Leaf color: Young expanding adaxial nearest RHS 138A, young expanding abaxial nearest RHS 138B; mature adaxial nearest RHS 137A, mature abaxial nearest RHS147B;

Foliage fragrance: Foliage and stem herbal fragrance;

Venation: Longitudinal; impressed on adaxial surface and costate on abaxial surface;

Vein color: Adaxial nearest RHS 137A and abaxial nearest RHS 147C;

Petiole: Micro-puberulent adaxial and abaxial; slightly concavo-convex; to about 4.5 mm long and 1.5 mm across at base; average about 3.5 mm long and about 1.5 mm across;

Petiole color: Adaxial nearest RHS 146B, abaxial nearest RHS 146C;

Stem: Micro-puberulent; quadrangular; mostly horizontal; about 64.0 cm long and 3.0 mm across at base; about 40 stems per plant; with compound branches in proximal nodes; about 6 branches per stem, branches to about 32.5 cm long and 2.0 mm across at base;

Stem color: Lower portion nearest RHS 146D, upper portion nearest RHS 146B;

Internodes: Average about 2.7 cm apart with greatest distance in the middle of the stem; about 9 to 14 nodes per stem before flowers;

Internode color: Same as surrounding stem;

Inflorescence: Cymosely clustered with many flowers typically branched at verticillasters in the 16 upper nodes; about 9 to 40 flowers per node and about 100 to 400 flowers per inflorescence stem or peduncle;

Peduncle: Flowering portion curving upwardly; flowers on one verticillaster flowering over prolonged period; flower portion in distal 32 cm and 4,5 cm wide;

Peduncle color: Nearest RHS N79A;

Pedicel: Sessile to 1.0 mm long and 0.3 mm diameter; puberulent; cylindrical; upwardly;

Pedicel color: When present nearest RHS N138C with moderate blush of nearest RHS N77C;

Flower bud: Curved clavate; about 9.0 mm long and 3.5 mm tall and 2.5 mm wide in bulb portion, 1.5 mm diameter at base; abaxial surface pubescent;

Flower bud color: Petal portion nearest RHS 86D with distal petal margins nearest RHS 86B; calyx portion nearest RHS 146B with heavy blush of nearest RHS N79B dorsal side and veins;

Flowers: Zygomorphic; perfect; bilabiate; sympetalous with basal 9.0 mm fused; lips opening to form about an 80 degree angle to each other; 12.0 mm long and 8.0 mm tall and 7.0 mm wide; in dense verticillasters;

*Upper lip.*—With two lobes; puberulent on abaxial surface, glabrous adaxial; lobes about 2.0 mm long and 2.0 mm wide above fusion; lobes with rounded apex; total size of lip about 12.0 mm long and about 5.0 mm wide at fusion.

*Lower lip.*—Consisting of three lobes; center and largest lobe slightly concave to flattened with rounded apex and crenate margin having seven indentations of about 1.0 mm deep in center and the three lateral incisions to about 0.5 mm deep; two side lobes with rounded apices and entire margin; center lobe to about 16.0 mm long in total, 7.0 mm long from fusion and up to 9.0 mm across when flattened; side lobes 2.0 mm long from fusion and 3.0 mm across; puberulent abaxial center and glabrous near margin, glabrous adaxial except pubescent tuft of white hairs nearest NN155D about 1.0 mm long in center.

*Petal color.*—Adaxial face upper lips nearest RHS N82C; lower lips nearest RHS N87C along margin with center nearest RHS 84D, and maculate with spots between about 0.2 mm and 0.3 mm diameter and in color nearest RHS 86A; adaxial and abaxial corolla tube nearest RHS 84D with spots or nearest RHS 86A decreasing in concentration and size to about 0.1 mm diameter proximally, and basal 1.0 mm nearest RHS NN155B; abaxial upper face nearest RHS N82D; abaxial lower lips nearest RHS N87C; abaxial tube nearest RHS 85C distally and nearest RHS 85D proximally with the basal 1.0 mm nearest RHS NN155B.

Calyx: Synsepalous; 5-merous fused into tube in basal 4.0 mm and separated in distal 2.0 mm; about 8.0 mm long and 3.0 mm diameter at apex and 2.0 mm diameter at base;

Sepals: Five; acute apex; basal fused; margin ciliolate; with about 3 conspicuous longitudinal veins; glabrous adaxial, pubescent abaxial; persistent; about 8.0 mm long and 1.0 mm across at fusion, fused in basal 6.0 mm and free in distal 2.0 mm;

Sepal color: Adaxial distally between veins nearest RHS 137A, proximally nearest RHS 138D and veins nearest RHS 137A, with distal region lightly blushed nearest RHS N79B; abaxial nearest RHS 146B with heavy blush of nearest RHS N79B dorsal side and veins;

Gynoecium: Single compound ovary with two carpels, single gynobasic style, and stigma bifid;

*Style*.—About 10.0 mm long and 0.5 mm diameter; color between RHS 70A and RHS NN155D.

*Stigma*.—Bifid in distal 1.0 mm to sharply acute apex; color between RHS 79A and RHS 83A.

*Ovary*.—Four-lobed, each lobe ovoid, about 1.0 mm long and 0.5 mm across, ovary color between RHS 145A and RHS N144D.

Androecium: Four;

*Filaments*.—Adnate to petals in basal 8.0 mm, free in distal 5.0 mm; cylindrical; straight; color between RHS N82C and RHS N82D.

*Anthers*.—Oblong ellipsoidal; 1.0 mm long and 0.3 mm across; color between RHS N92B and RHS N92C.

*Pollen*.—Abundant; color nearest RHS 158B.

Flowering period: In Western Michigan beginning early June for six weeks and repeating into October; individual flowers remain open for about three days;

Flower fragrance: None detected;

Flower attitude: Outwardly;

Fruit and seed: Rare, nutlets, flattened, round; about 1.5 mm diameter and 0.5 mm thick; nearest RHS 200B;

Pest and disease susceptibility: No resistance beyond that which is typical for *Nepeta* but typically not prone to browsing by deer or rodents.

I claim:

1. A new and distinct hardy perennial *Nepeta* plant named 'Picture Purrfect' essentially as herein described and illustrated useful for landscaping as a specimen, en masse, or in a container to bring color and fragrance to a garden and attract butterflies and hummingbirds.

* * * * *